US008113007B2

(12) United States Patent
Zenobi et al.

(10) Patent No.: US 8,113,007 B2
(45) Date of Patent: Feb. 14, 2012

(54) APPARATUS AND METHOD FOR RECEIVING, STORING AND DISTRIBUTING BLOOD BAGS

(75) Inventors: Mauro Zenobi, Bastia Umbra (IT); Simone Ventura, Campello sul Clitunno (IT); Cristiana Neri, Bastia Umbra (IT)

(73) Assignee: Angelantoni Industrie SpA, Massa Martana (IT)

( * ) Notice: Subject to any disclaimer, the term of this patent is extended or adjusted under 35 U.S.C. 154(b) by 633 days.

(21) Appl. No.: 11/575,984

(22) PCT Filed: Sep. 29, 2004

(86) PCT No.: PCT/IT2004/000536
§ 371 (c)(1),
(2), (4) Date: Mar. 26, 2007

(87) PCT Pub. No.: WO2006/035465
PCT Pub. Date: Apr. 6, 2006

(65) Prior Publication Data
US 2008/0104993 A1  May 8, 2008

(51) Int. Cl.
*F25D 25/00* (2006.01)
(52) U.S. Cl. .................................. 62/62; 62/383; 62/440
(58) Field of Classification Search .............. 62/62, 440; 235/383
See application file for complete search history.

(56) References Cited

U.S. PATENT DOCUMENTS

| 4,441,329 A | 4/1984 | Dawley |
| 5,520,450 A | 5/1996 | Colson, Jr. et al. |
| 5,661,978 A | 9/1997 | Holmes et al. |
| 5,842,179 A * | 11/1998 | Beavers et al. ................. 705/28 |
| 6,109,053 A | 8/2000 | Strackbein |
| 6,453,687 B2 | 9/2002 | Sharood |
| 6,688,123 B2 | 2/2004 | Felder |
| 7,527,764 B2 | 5/2009 | Angelantoni et al. |

FOREIGN PATENT DOCUMENTS

| DE | 44 18 005 A | 11/1995 |
| DE | 197 16 913 A1 | 11/1998 |
| DE | 103 11 246 A1 | 9/2004 |

(Continued)

OTHER PUBLICATIONS

Machine translation of Taguchi et al. JP Publication No. 06-343679.*
Machine translation of Hirota et al. JP Publication No. 2000-116767.*
English-language abstract for ITUD960073 (Angelantoni).
PCT International Search Report dated Nov. 10, 2004 for PCT/IT2004/000048, 3 pages.

(Continued)

*Primary Examiner* — Cheryl J Tyler
*Assistant Examiner* — Jonathan Koagel
(74) *Attorney, Agent, or Firm* — Fredrickson & Byron, P.A.

(57) ABSTRACT

Method and apparatus (1) for receiving, storing and distributing blood bags including a cabinet (2) for containing all the components of the apparatus (1); a refrigerated space (21) for containing the bags; a magazine (3) housed inside the refrigerated space (21) comprising a plurality of cells (31), each capable of containing a single bag, each of the cells being identified by a cell code. The apparatus (1) further includes a data processing system (7) housed inside the cabinet (2), capable of controlling a movement system (5) and a cooling system (6) each housed inside the cabinet (2), and capable of controlling the receiving, the preservation and the releasing of the bags, and capable of exchanging data from and to an external data-management system (17) with which the apparatus (1) can interact.

13 Claims, 3 Drawing Sheets

FOREIGN PATENT DOCUMENTS

| | | |
|---|---|---|
| IT | UD 960 073 A1 | 11/1997 |
| JP | 06304230 | 11/1994 |
| JP | 06343679 | 12/1994 |
| JP | 2000-116767 * | 4/2000 |
| JP | 2003093476 | 4/2003 |
| RU | 2 129 882 C1 | 5/1999 |
| RU | 2 220 447 C2 | 12/2003 |
| WO | WO 9741525 A1 * | 11/1997 |
| WO | WO 99/18528 A | 4/1999 |
| WO | WO 02/100462 A | 12/2002 |
| WO | WO 2004/028572 A | 4/2004 |
| WO | WO 2005/075006 A1 | 8/2005 |

OTHER PUBLICATIONS

PCT Written Opinion dated Nov. 10, 2004 for PCT/IT2004/000048, 5 pages.
PCT International Preliminary Report on Patentability dated Dec. 5, 2005 for PCT/IT2004/000048, 10 pages.
Office Action for U.S. Appl. No. 10/588,387, dated Jun. 4, 2009, 25 pages.
Response to Office Action mailed Jun. 4, 2009 for U.S. Appl. No. 10/588,387, filed Sep. 4, 2009, 10 pages.
Notice of Allowance for U.S. Appl. No. 10/588,387, dated May 12, 2010, 9 pgs.

* cited by examiner

APPARATUS AND METHOD FOR RECEIVING, STORING AND DISTRIBUTING BLOOD BAGS

RELATED APPLICATIONS

This application claims priority to International Application No. PCT/IT2004/000536, filed Sep. 29, 2004, the teachings of which are incorporated herein by reference.

The present invention refers to an automated and computerised apparatus and to a method for receiving, preserving and releasing blood bags.

The company Angelatoni developed an apparatus of this type: this consisted substantially of a refrigerator inside which there is a rotating magazine equipped with cells for containing blood bags blood; the refrigerator is locally controlled by a local electronic computer (so called Personal Computer or PC) by way of a series of electrical connections. An electrical connection is provided for each sensor and an electrical connection for each actuator; all the electrical connections are grouped in two large multi-wire cables.

The approach followed in the designing of that apparatus is the conventional one, which is used when a computerised machine-tool is designed: that is to say, the mechanics are separated from the electronics and the sensors and actuators are placed at the interface. Such an approach could be very sensible; in fact, the mechanics and the electronics have little in common; in general there is no advantage in placing them close to one another (on the contrary, it may be difficult), and it is quite often necessary to keep them distant from each other. The PC is of conventional type and therefore it is very easy to load software of commercial type as well as the developed one.

Recently, Angelantoni decided to carry out some research activity in order to improve both the older version of the apparatus and software thereof. Therefore a suitable control program was developed and loaded onto a data processing system (which can be advantageously a PC) of the apparatus.

As a result of this activity, it was realised that such an apparatus for blood bags is very different from a computerised machine tool.

Firstly, its principal activity (that is to say, preserving the blood bags at the correct temperature) is carried out in the absence of an operator.

This activity is very important and therefore safety and reliability of the apparatus are key factors.

The apparatus is typically placed in locations with free access, so there is the need for the access to the blood bags to be carefully controlled. Also, every operation regarding movements of the bags should be tracked and saved as a "history" document.

Since possible malfunctions and errors of such an apparatus (in the receiving and/or preservation and/or release of the blood bags) may have very serious consequences regarding the life not only of one but also of several human beings, such apparatus must be very reliable and free from system crashes.

Also, such an apparatus should not be a closed system, but should be instead able to exchange data with the environment it is working in, in order to retrieve external information about the blood bags to be stored/drawn and to give information about the same bags upon a remote request.

The present invention arises from these observations. The aim of the present invention is to provide an apparatus for receiving, preserving and releasing blood bags that is a stand-alone unit capable of fully managing its own functions and interacting with its external working environment to exchange key data.

This aim is substantially achieved by the apparatus having the characteristics disclosed in independent claim 1. Advantageous features of the present invention are disclosed in the dependent claims.

Another aim of the present invention is to provide a method for receiving, preserving and releasing blood bags that is capable of overcoming all the drawbacks of the prior realizations.

The ideas underlying the present invention are
- to enclose all the components of the apparatus, including the data-processing system, in a single cabinet, in order for the apparatus to be compact and safer;
- to provide the apparatus with a computerized control system which autonomously manages the functions of the apparatus;
- to provide the apparatus with data processing and logic means (advantageously by means of a control program) to exchange key data from and to an external data management system, with which the apparatus according to the invention can interact, and to store said data in a memory. In particular, said data concern the bag and the blood contained therein.

The method according to the invention is a method for receiving, preserving and releasing blood bags in a temperature and closure controlled apparatus provided with at least one interface to interact with an user, comprising the steps of:
- providing the blood bags with coded-identification means which also comprise data concerning the blood contained in the same bag;
- before receiving in said apparatus or drawing therefrom a bag, obtaining from said coded-identification means the data concerning the blood contained in the bag and storing them in a memory.

The present invention will become clear from the following description to be considered in conjunction with the appended drawings, in which.

Figure 1:
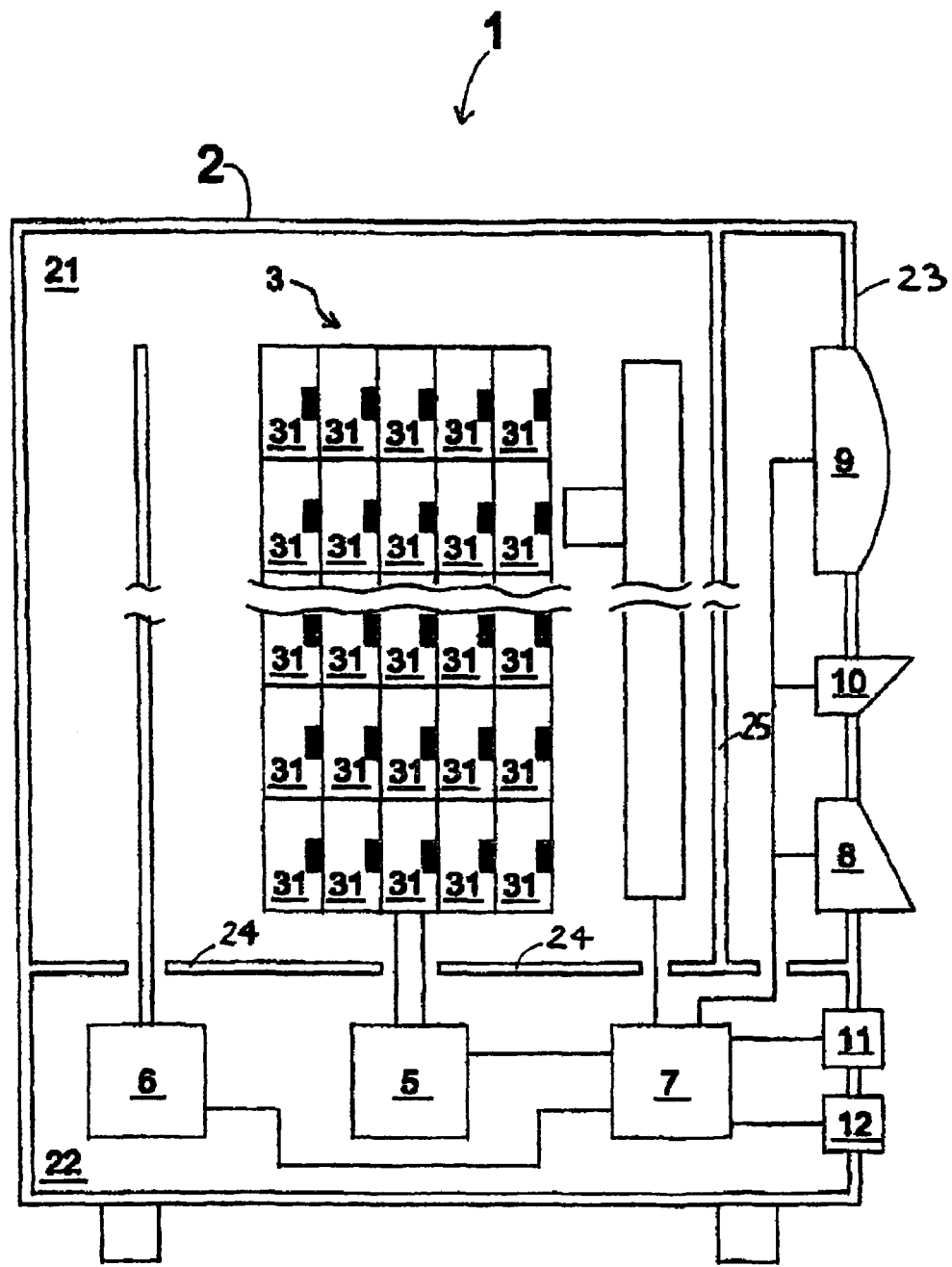
FIG. 1 shows the simplified internal block diagram of an exemplary embodiment of an apparatus according to the present invention.
Figure 2:
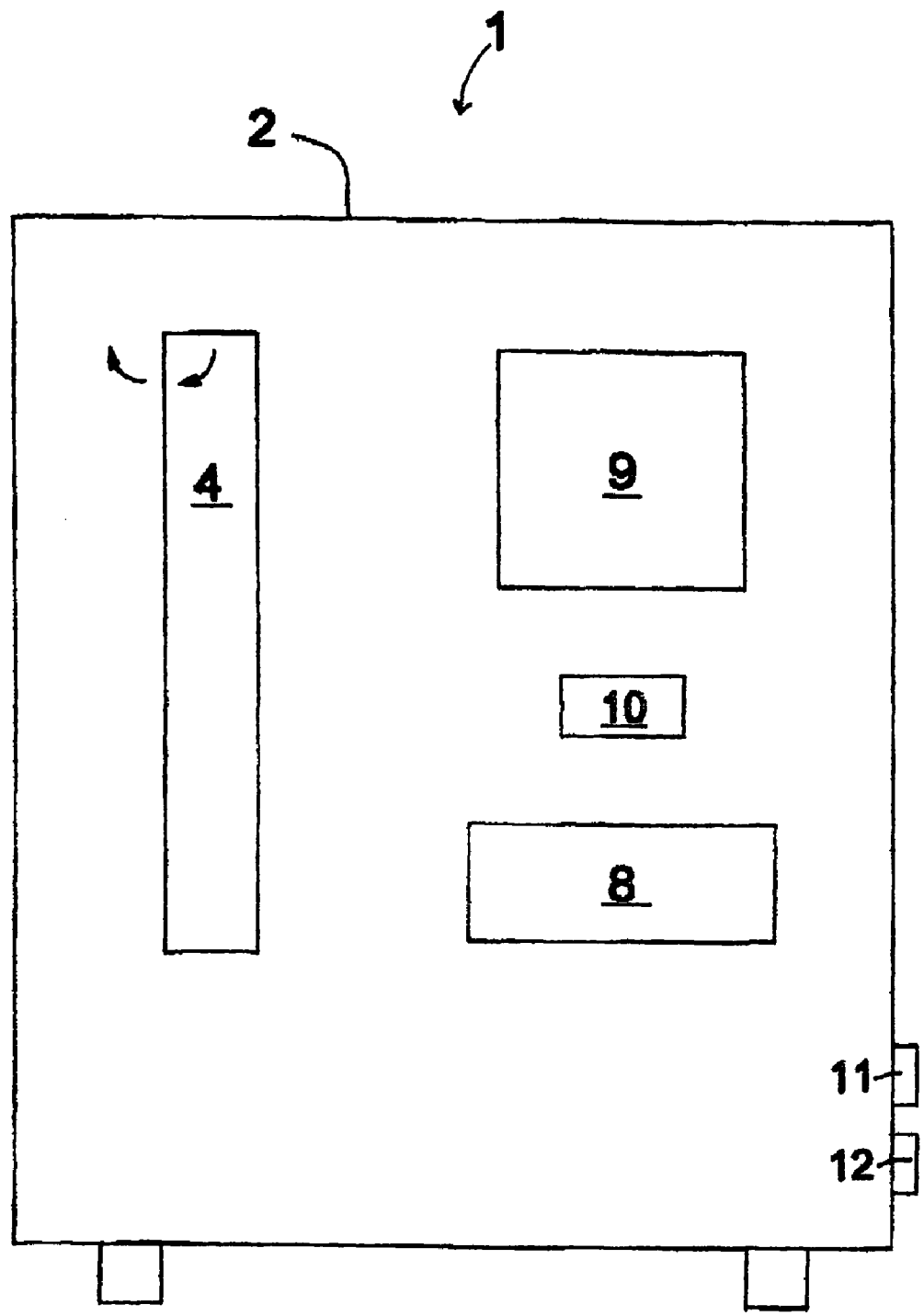
FIG. 2 shows a diagrammatic front view of the apparatus in FIG. 1.

The present invention will be described below with reference to the figures; such reference is not to be understood in a restrictive sense but purely by way of explanation. The apparatus according to the present invention, indicated as a whole by 1 in the figures, is intended for receiving, preserving and releasing blood bags. It comprises a cabinet 2 for containing all the components of the apparatus 1, divided by a separating wall 24 in:
- a refrigerated space 21 for containing the bags, in which there is a magazine 3 comprising a plurality of cells 31, each capable of containing a single bag, each of the cells 31 being identified by a cell code;
- a service machinery space 22 comprising:
- a movement system 5 capable of moving, preferably rotating, the cells 31; a cooling system 6 capable of cooling the refrigerated space 21;
- a data-processing system 7 capable of controlling the movement system 5 and the cooling system 6, and capable of controlling the receiving, the preservation and the releasing of the bags; and also capable of exchanging data regarding the blood bags from and to the external environment (see FIG. 4).

The apparatus 1 further comprises at least one door 4 for allowing access by an operator to the cells 31 and a keyboard 8 and a screen 9, both connected to the processing system 7, and both placed at the frontal wall 23 of the cabinet 2. A further wall 25 is used to isolate the frontal wall 23 from the refrigerated space 21.

The apparatus naturally requires an electrical supply system for its electrical components, in particular the movement system 5, the cooling system 6 and the processing system 7. The supply system requires an electric power source; typically, this source consists of the mains electrical system; in addition, a battery (or a similar component) may advantageously be provided so that the apparatus is operational even when there is no mains power (neither the electrical supply system nor the electric power sources are illustrated in the figures).

The apparatus 1 according to the present invention having the characteristics illustrated above is safe and reliable.

With respect to the previous apparatus, there are no cables which could be accidentally detached and therefore compromise its operation; therefore it is more reliable.

Since the data processing system 7 is inside the cabinet 2, it is much more difficult to tamper with compared with the previous apparatus and is therefore safer. The only cable necessary is the supply cable; therefore the apparatus 1 is very easy to move. Even if the supply cable were to be disconnected, the replacement operation is trivial and may be performed by anyone.

Since all the components of the apparatus 1 are contained in the cabinet 2, its design may of course be more studied, this being an important element nowadays for any machine, in particular for machines which must be positioned in public places.

With regard to the screen 9 and the keyboard 8, these have been placed at the wall 23 of the cabinet 2 so as not to take too much room from the refrigerated space 21; the screen 9 may advantageously be of the flat type; the keyboard 8 may advantageously be of the flat type; the screen 9 and the keyboard 8 could also be incorporated in a "touch screen"; in FIG. 1, the keyboard 8 protrudes a little (for example by 10 cm) with respect to the flat surface of the wall 23 of the cabinet 2; alternatively, the apparatus 1 may be produced in such a manner that neither the screen 9 nor the keyboard 8 protrude in the slightest from the wall 23 of the cabinet 2.

In FIG. 1, the cooling system 6 (generally composed of an evaporator 6A, a compressor and a condenser, these two not shown) is shown very diagrammatically; the evaporator 6A inside the refrigerated space 21 may be noted.

The processing system 7 is capable of precisely controlling the receiving, the preservation and the releasing of the bags by means of the cell codes; in fact, this system knows the contents of the various cells.

In order to succeed in incorporating to the optimum extent (without the dimensions of the cabinet 2 becoming excessive) all the components inside a single cabinet 2, it was necessary to solve a series of technical problems.

Nowadays, blood bags are generally provided with bag identification means; such means often consist of one or more bar codes; recently, bags provided with electronic tags, termed RFID (Radio Frequency Identifier) have been studied and experimented with.

To benefit from this characteristic of the blood bags, it is advantageous to provide a reading device 10 for reading bag identification means; the device 10 is connected to the processing system 7, housed inside the cabinet 2 and placed at the wall 23 of the cabinet 2; in this way, both when the operator loads a new blood bag into the apparatus 1 and when the operator unloads a blood bag from the apparatus 1, the recording of the operation by the processing system 7—as it will be more precisely described hereinafter—takes place automatically, therefore simply and safely.

According to the preferred exemplary embodiment of the figures, the cells 31 are structured in superposed levels, for example, five levels composed of ten cells.

In this case it is particularly advantageous to provide for the cell code to be univocal for the whole magazine; in fact, in this way it is not possible to confuse the cells with one another. Alternatively, the cell could be distinguished by a cell code and by a level code; in this case, however, if an error should occur in the level code during the processing phase, there would be confusion between cells.

For constructional purposes, it is advantageous to provide for the cell code to be independent of the level in which the cell is located and of the position of the cell in the level; for example, the cells of the magazine could be associated with a series of random codes all different from one another; in fact, in this way, constructional errors would not have repercussions on the operation of the apparatus, as will become clear from the following description.

It is preferable to provide for the placing, at the cells 31, of cell identification means 32 capable of retrieving and/or containing cell codes; in FIG. 1 the means 32 are shown by means of small black rectangles adjacent to the right-hand side of each cell; the means 32 may very simply and very effectively be bar codes; alternatively, electronic tags could be used.

In the case of bar codes, these will be applied to the cells in the stage of construction of the apparatus 1.

If it is selected that the cell codes should be independent of the position and of the level, the bar codes will also be independent of the position and of the level, and therefore the construction of the machine will be correct however they are applied to the cells. In this case, before normal operation, the processing system 7 of the apparatus must determine the association between cells and cell codes.

If cell identification means 32 are provided, the apparatus may advantageously comprise at least one reading device 132 for reading cell identification means 32 and which is connected to the processing system 7, and at least one corresponding movement member 131 for said reading device 132 controlled by the processing system 7; in this case the device 132 and the member 131 are housed inside the refrigerated space 21; the whole consisting of the device 132 and the member 131 constitutes a reading system 13 for reading cell identification means.

Such a solution is advantageous when the cost of the reading device 132 is considerable; in addition, this allows optimum positioning of the reading device 132 with respect to the identification means 32.

In FIG. 1, the member 131 is capable of translating the device 132 vertically and positioning it at the five positions of the identification means 32 of the cells of each level.

As already mentioned, it is advantageous to provide a service machinery space 22 separated from the refrigerated space 21 and which contains the movement system 5, the cooling system 6 and the processing system 7.

In this way, there can be placed in the refrigerated space 21 only what effectively requires to be refrigerated, that is to say, the blood bags; some components cannot necessarily be taken out of the refrigerated space: the evaporator 6A, the cell magazine 3 and any reading system for reading cell identification means 132.

Advantageously, a metal container may be provided, capable of completely containing the processing system 7; this metal container is not specifically illustrated in the figures; the purpose of such a container is to shield and insulate the processing system 7.

The magazine 3 of the apparatus 1 according to the present invention may be produced in many different ways; the rotation may be with respect to a vertical axis, as in the example of FIG. 1, or with respect to a horizontal axis; the movement of the cells may also be constituted by a combination of rotation and translation. Different embodiments may also be provided for the door or doors for access to the cells of the magazine 3.

According to the example of the figures, the apparatus 1 comprises a door 4 which extends from the first to the last level of the magazine 3, wherein one cell of each level is notional, and wherein the movement system 5 is capable of rotating a single level at a time; in this way, when the apparatus 1 is in the rest phase, the five notional cells are at the door 4, and therefore if the door 4 is opened it is not possible to access any blood bag; when an operator sends to the apparatus 1 a request for loading or unloading a blood bag, the processing system 7 rotates one of the levels of the magazine 3 and brings one of its cells to the door so that the operator can insert or withdraw the blood bag.

According to an alternative example (not shown), the apparatus 1 comprises a number of doors equal to the number of levels of the magazine 3, the movement system 5 is capable of rotating the whole magazine 3, and the processing system 7 is capable of releasing the opening of a single door at a time during normal operation.

This alternative example requires simpler mechanics for the magazine movement system, but more complicated mechanics for the doors.

To increase the reliability of the apparatus 1, it is advantageous to provide for the processing system 7 to comprise a sub-system 7A (see FIG. 4) for thermal control of the refrigerated space 21, and for the sub-system 7A to be independent of, but in communication with, the processing system 7. In this way, even if the processing system 7 has problems, the thermal control is maintained; this is very useful for safeguarding the contents of the blood bags.

To increase further the reliability of the apparatus 1 it is advantageous to provide for the sub-system 7A an emergency power supply (for example a battery); this is very useful to keep safe the blood bags.

Figure 4:
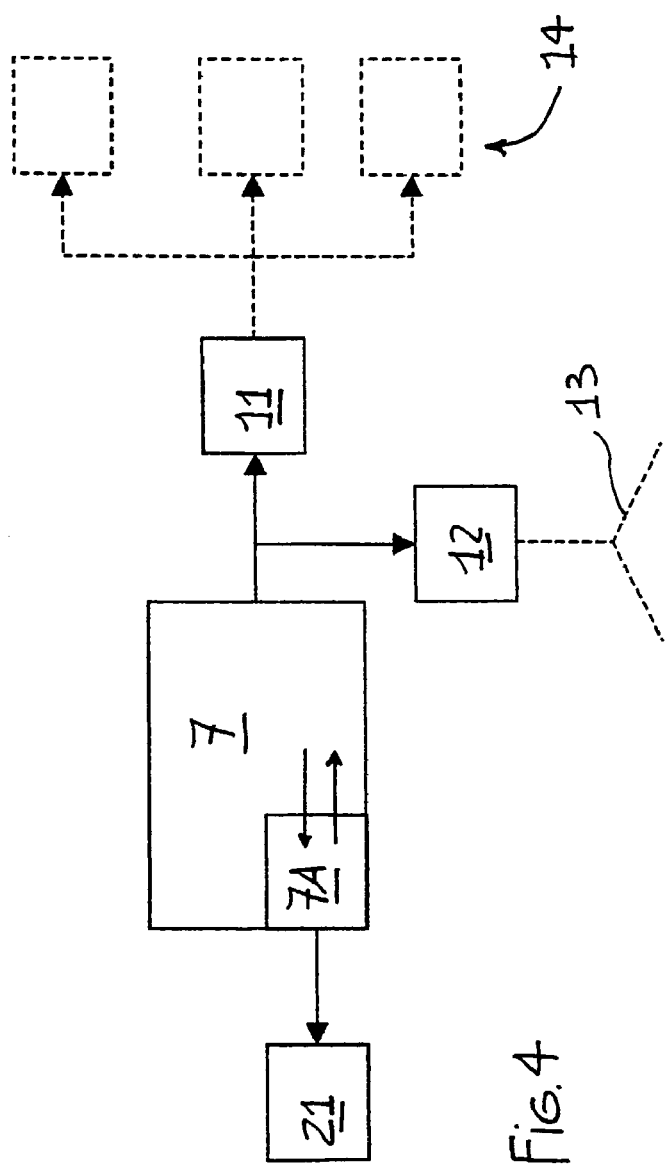
FIG. 4 shows a logic connection between a data-processing system according to the present invention and some external data-system.

The apparatus 1 according to the present invention can carry out its principal activity on its own, but it is to be noted that it can connect to other apparatuses 1 by means of, for example, a computer network 14 and/or a telephone network 13, in order to let it exchange data to and from the said other apparatuses (see FIG. 4).

The apparatus 1 may comprise, for example, a network port 11 for connecting the processing system 7 to a computer network 14 (shown in dashed lines in FIG. 4); advantageously, in the light of the need to limit the cables, the network port 11 is of the wire-free type. The apparatus 1 may comprise, for example, a modem 12 for connecting the processing system 7 to a telephone network 13 (shown in dashed lines in FIG. 4); advantageously, in the light of the need to limit the cables, the modem 12 is of the wire-free type (GSM modem or, in future, UMTS).

The apparatus 1 may therefore also be connected to the INTERNET by way of the network port 11 and/or the modem 12

The processing system 7 is typically and advantageously provided by means of a computer; this requires a suitable program 18. Such a program will have functions for controlling the apparatus 1, and management functions, as it will be apparent from the following description (see FIG. 3).

Figure 3:
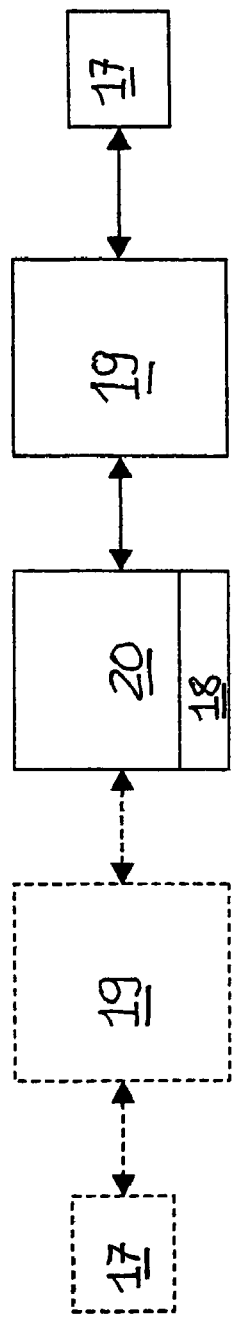
FIG. 3 shows a logic connection between a program module according to the present invention and an external data systems.

Even if it could work as a closed system, the apparatus 1 according to the present invention is typically placed in a hospital or the like, where it is able to be connected to the management-system of the hospital and, in other words, have the program 18 of the apparatus 1 communicate with the hospital management program 17 (see FIG. 3). This communication may regard all the information relative to the blood bags, i.e. the blood type, and movements of the same bag, i.e. the operator who withdrew/stored the last bag, etc.

In order so to do, it is advantageous to provide for the data processing system 7 (see FIG. 3) to comprise a control program 18 equipped with a communication module 19 capable of communicating with a management program 17, typically by way of a network port. In this way, all the program code which refers to the communication with the management program 17 is grouped together.

It is furthermore advantageous to provide for the communication module 19 to be a software element independent of the control program 18 and to be capable of being actuated by the control program 18 during the execution of the control program 18 itself.

In this way, if it is necessary to apply modifications to the communication module 19 it is not necessary to rewrite the program 18 but it is sufficient to recompile the module 19.

Such a communication module 19 may be constituted, for example, by a "DLL". Such a communication module may be produced, for example, by means of the "COM" technology or by means of the ".NET" technology; both these technologies have been developed by Microsoft.

To facilitate communication of the apparatus 1 with different hospital management programs 17, provision may be made for the control program 18 to be equipped with a software interface 20 that is fixed and predetermined for interacting with the communication module 19; in this way, the various communication modules 19 may be developed on the basis of this interface 20 independently of the program 18 of the apparatus 1. This means that the core of the control program 18 may always remain the same while the communication modules 19 can be changed according to, and to comply with, the hospital data management system 17. According to the client's requirements, the apparatus 1 will be supplied with its own control and management program 18 and with the communication module 19 suited to the information system of the hospital or other working places.

It must be emphasised that the control program 18 according to the present invention enables a new variety of advantages on apparatuses for blood preservation. First of all, every operation (for example load or unload of a blood bag) regarding the apparatus 1 must be submitted to verification and authentication. This means that the access to the bags shall be granted after inserting (through the keyboard 8 for instance) a valid key-word (password) or digital signature or after some other form of acknowledgement. On this basis, the system manager can choose which operation should be allowed or not, and to whom.

Every operation and author thereof are stored in a non-volatile memory (advantageously in a file .log or, more safely, in a Database Management System (DBS)) to track the history of every blood bag and the actions of each operator. It is clear that this kind of management greatly enhances the control of the blood preservation, avoiding wanted or unwanted tampering, thereby providing a safer preservation.

Even before authentication, every operation on the apparatus 1 has to be cross-checked up with the hospital management program 17. Indeed, the sequence of steps needed to draw/store a blood bag may be the following:

A1) the operator must introduce in the apparatus 1 his/her correct password thereby gaining control of the apparatus;

A2) for the drawing, the hospital data management system provides an operator with a coded (for example bar-coded) request;

A3) the control program 18 then performs a reading of the code of the request (for example by means of the reading device 10) and cross-checks the validity of the request itself by asking an acknowledgment to the hospital data management system 17 through the communication module 19;

A4) after receiving an affirmative acknowledgment, the control program 18 calls for the reading of the code printed on the bag itself and cross-checks it with the code previously acquired from the request: if the two codes match the operator is enabled to conclude the drawing; in case of an operation of storing, the code, containing key data, of the bag to be stored is read by means of the reading device 10;

A5) the operation (drawing or storing) and data concerning the involved bags are logged in a "history" file (.log file or a DBS) which is stored locally on the apparatus 1 but it is readable by the hospital management system 17 through the communication module 19.

It is clear that through the A3÷A4 phases it is possible for example to check the condition of the patient to which the bag is going to be delivered, and/or to check the bag's expiry date, in order to allow only secure and permitted operations. Only after all the checks have been passed the operator gains free way to the blood bags.

Also, the blood bags can be arranged by the control program 18 in accordance with blood type, expiry date, destination and intended use thereof. The operator, however, for privacy reasons cannot gain access to the hospital's database to find information about the bag he/she is going to draw. Another possible feature of the control management program 18 may be to detect whether the bags of a particular blood type are over, thereby generating an automatic warning message and speeding up the procedures of blood search and supplying.

Another useful feature provided with the control program 18 according to the present invention is the management of the blood supply. This means it is possible to set a minimum number (threshold) of bags (a minimum supply) for a specific blood type which must always be present in the apparatus 1, for emergency reasons. Upon requesting a blood bag belonging to the set minimum supply, the drawing is denied and a message is displayed to the operator. Of course the threshold may be accommodated by the system manager. It is also possible, in emergency cases, to enable a procedure to access the bags belonging to the minimum supply.

Thanks to the connections towards the external environment (the modem 12 or the network port 11), two or more apparatuses 1 object of the present invention can be used to work together, thereby expanding the blood storage capability, by linking them together to each other and/or to the hospital data management system 17.

Each apparatus 1 may be recognised through an individual code, and the same may be applied to the blood bags, which this way are univocally assigned thereto. Clearly from an apparatus 1 it is possible to poll every other apparatus 1 for retrieving any useful information (blood content of the apparatus 1, remote supervision of the operation actually performed on a particular apparatus 1, etc.), eventually showing it to the operator. This way the system manager, and/or a highly qualified person, can remotely monitor and/or guide the usually less experienced operators. Also, remote control of an apparatus 1 from another one can be implemented. For example it is possible to send commands (control of the movement system 5, locking/unlocking of the door 4, etc.) to an apparatus 1 from a remote location, being however necessary an operator near the controlled apparatus.

It is understood that all the variants of the invention described, as also the equivalent ones which do not depart from its inventive concept, are contained in the protective scope of the following claims.

The invention claimed is:

1. A method for receiving, preserving and releasing blood bags in a temperature and closure controlled apparatus having a plurality of cells each capable of containing a single bag and provided with a movement system permitting controlled access to only one cell at a time and with at least an interface for interacting with an user, comprising the steps of:
   (a) providing the blood bags with coded-identification means which also comprise data concerning the blood contained in the same bag;
   wherein in a receiving stage,
   (b) before receiving in said apparatus a bag, obtaining from said coded-identification means the data concerning the blood contained in the bag and storing them in a memory,
   (c) exchanging the data concerning the blood contained in the bag with a data-management system external to said apparatus, and
   (d) allowing an user to insert the bag in an empty cell of the plurality; and
   wherein in a releasing stage, before permitting a specific bag of blood to be drawn from said apparatus,
   (e) providing the user with a coded request that is separate from an user acknowledgement for interacting with the interface, the code request being univocally associated with such specific bag of blood, the coded request being emitted on a basis of data contained in the external data-management system and referring to such specific bag of blood,
   (f) checking the coded request, and
   (g) enabling the movement system of the apparatus to allow the user to draw the specific bag of blood only from the cell containing the bag of blood as specified according to the coded request.

2. The method according to claim 1, wherein the operations on said apparatus, in particular the drawing or the storing of bags, are subordinate to a procedure for acknowledgment of the user through said interface.

3. The method according to claim 2, wherein said procedure for acknowledgment involves the inserting of a keyword.

4. The method according to claim 2, wherein the data concerning the blood contained in the bag are cross-checked with corresponding data present in the external data-management system.

5. The method according to claim 4, further comprising for the drawing of the bag the steps of:

(a) performing a reading of the code of the request and cross-checking the validity of the request itself by asking an acknowledgment to the external data-management system; and (b) only after receiving an affirmative acknowledgment, calling for the reading of the coded-identification means and cross-checking with a code previously acquired from the request enabling the user to conclude the drawing on the basis of the result of the cross-check.

6. The method according to claim 1, wherein the data concerning the blood contained in the bag are used to check the compatibility of the blood with a patient to whom the bag is going to be delivered by checking said data in the external data-management system.

7. The method according to claim 1, wherein the data concerning the blood contained in the bag are used to check the blood's expiry date.

8. The method according to claim 1, wherein the data concerning the blood contained in the bag are used to arrange the bags inside said apparatus in accordance with blood type, expiry date, destination and intended use of the blood.

9. The method according to claim 1, wherein the data concerning both particular blood type and the bags containing it are used to generate a signal of lack of bags and/or to identify a minimum supply of bags containing blood of said blood type.

10. The method according to claim 9, wherein the drawing of a bag whose blood type belongs to said minimum supply is denied.

11. The method according to claim 1, wherein two or more apparatuses are linkable together in order to exchange data concerning the blood contained in the apparatuses.

12. The method according to claim 11, wherein from a remote apparatus another apparatus is remotely monitored and/or controlled and/or an operator thereof is guided.

13. A method for receiving, preserving and releasing blood bags in a temperature and closure controlled apparatus having a plurality of cells each capable of containing a single bag and provided with a movement system permitting controlled access to only one cell at a time and with at least an interface for interacting with an user, comprising the steps of:

(a) providing the blood bags with coded-identification means which also comprise data concerning the blood contained in the same bag;

wherein in a receiving stage, (b) before receiving in said apparatus a bag, obtaining from said coded-identification means the data concerning the blood contained in the bag and storing them in a memory, (c) exchanging the data concerning the blood contained in the bag with a data-management system external to said apparatus, and (d) allowing an user to insert the bag in an empty cell of the plurality; and wherein in a releasing stage, before permitting a specific bag of blood to be drawn from said apparatus, (e) providing the user with a coded request that is separate from an user acknowledgement for interacting with the interface, the code request being univocally associated with such specific bag of blood, the coded request being emitted on a basis of data contained in the external data-management system and referring to such specific bag of blood, (f) performing a reading of the code of the request and cross-checking the validity of the request itself by asking for an acknowledgement from the external data-management system, and only upon receiving an affirmative acknowledgement, (g) enabling the movement system of the apparatus to allow the user to draw the specific bag of blood only from the cell containing the bag of blood as specified according to the coded request, and (h) calling for reading of the coded-identification means on the drawn bag and cross-checking with a code previously acquired from the coded request enabling the user to conclude drawing the specific bag of blood on basis of result of the cross-check.

* * * * *